(12) United States Patent
Kunieda et al.

(10) Patent No.: US 9,750,776 B2
(45) Date of Patent: Sep. 5, 2017

(54) AGENTS FOR PROMOTING SECRETION AND/OR SUPPRESSING DECREASE OF ADIPONECTIN

(75) Inventors: Yukiko Kunieda, Tokyo (JP); Tomohiro Hosoya, Saitama (JP); Shun Obuchi, Saitama (JP); Tsuguaki Nishiya, Tokyo (JP); Joelle Reitz, les Essarts le roi (FR); Christine Martin Rouas, Noisy le Roi (FR); Remi Perrin, Lucé (FR); Philippe Marchal, Rennes (FR)

(73) Assignees: MEGMILK SNOW BRAND CO., LTD., Sapporo (JP); SAVENCIA SA, Viroflay (FR)

( * ) Notice: Subject to any disclaimer, the term of this patent is extended or adjusted under 35 U.S.C. 154(b) by 0 days.

(21) Appl. No.: 12/920,844

(22) PCT Filed: Mar. 9, 2009

(86) PCT No.: PCT/JP2009/054973
§ 371 (c)(1),
(2), (4) Date: Sep. 3, 2010

(87) PCT Pub. No.: WO2009/110646
PCT Pub. Date: Sep. 11, 2009

(65) Prior Publication Data
US 2011/0020389 A1 Jan. 27, 2011

(30) Foreign Application Priority Data
Mar. 7, 2008 (JP) .................................. 2008-058560

(51) Int. Cl.
| | | |
|---|---|---|
| A61K 35/74 | (2015.01) |
| A61K 36/06 | (2006.01) |
| A61K 35/744 | (2015.01) |
| A61K 35/747 | (2015.01) |
| A23K 10/18 | (2016.01) |
| A23K 50/40 | (2016.01) |
| A23L 33/135 | (2016.01) |

(52) U.S. Cl.
CPC .............. *A61K 36/06* (2013.01); *A23K 10/18* (2016.05); *A23K 50/40* (2016.05); *A23L 33/135* (2016.08); *A61K 35/744* (2013.01); *A61K 35/747* (2013.01)

(58) Field of Classification Search
None
See application file for complete search history.

(56) References Cited

U.S. PATENT DOCUMENTS

| | | | |
|---|---|---|---|
| 6,132,786 A * | 10/2000 | Poulos et al. ................. 426/326 |
| 6,827,953 B1 * | 12/2004 | Mizutani et al. ............... 426/62 |
| 7,763,281 B2 * | 7/2010 | Chen ....................... A23C 9/127 |
| | | | 424/535 |
| 8,642,318 B2 * | 2/2014 | Kawakami et al. ....... 435/252.9 |
| 2002/0048757 A1 * | 4/2002 | Mori et al. ......................... 435/6 |
| 2005/0142166 A1 * | 6/2005 | Flambard .............. A23L 1/3053 |
| | | | 424/439 |
| 2005/0180963 A1 * | 8/2005 | Adams et al. .............. 424/93.45 |
| 2005/0244426 A1 * | 11/2005 | Sawada et al. .......... 424/195.16 |
| 2006/0241042 A1 * | 10/2006 | Kitamoto et al. ............... 514/12 |
| 2010/0278794 A1 | 11/2010 | Kunieda et al. |

FOREIGN PATENT DOCUMENTS

| | | | |
|---|---|---|---|
| EP | 2 011 500 | | 1/2009 |
| JP | 59-225120 | | 12/1984 |
| JP | 2-42962 | | 2/1990 |
| JP | 6-319447 | | 11/1994 |
| JP | 8-268899 | | 10/1996 |
| JP | 10-298083 | | 11/1998 |
| JP | 2000-197469 | | 7/2000 |
| JP | 2001-302523 | | 10/2001 |
| JP | 2003-95963 | | 4/2003 |
| JP | 2003-252770 | | 9/2003 |
| JP | 2003-306436 | | 10/2003 |
| JP | 2004-99539 | | 4/2004 |
| JP | 2004-315477 | | 11/2004 |
| JP | 2005-60308 | | 3/2005 |
| JP | 2005-68132 | | 3/2005 |
| JP | 2005154432 A | * | 6/2005 |
| JP | 2005-270066 | | 10/2005 |
| JP | 2006-69993 | | 3/2006 |
| JP | 2006076961 A | * | 3/2006 |
| JP | 2006-131512 | | 5/2006 |
| JP | 2006-193501 | | 7/2006 |
| JP | 2006-193502 | | 7/2006 |
| JP | 2006-238743 | | 9/2006 |
| JP | 2006-244377 | | 9/2006 |
| JP | 2006-335702 A | | 12/2006 |
| JP | 2007-39423 | | 2/2007 |
| JP | 2007-195444 A | | 8/2007 |
| JP | 2007-254448 | | 10/2007 |
| JP | 2007-261993 | | 10/2007 |
| JP | 2007-320900 | | 12/2007 |
| WO | 01/88095 A1 | | 11/2001 |
| WO | WO 2005/112987 | * | 12/2005 |
| WO | WO 2008/012947 A1 | * | 1/2008 |

OTHER PUBLICATIONS

Border (Biotechnology Letters (1987), vol. 9, No. 12, pp. 843-848).*
Lopes da Costa (Chem. Eng. Technol. (1998), vol. 21, pp. 354-356).*

(Continued)

*Primary Examiner* — Susan Hoffman
(74) *Attorney, Agent, or Firm* — Greenblum & Bernstein, P.L.C.

(57) ABSTRACT

To provide an agent promoting secretion and/or suppressing decrease of adiponectin, and an eating and drinking product and a feed promoting secretion and/or suppressing decrease of adiponectin. Provided are an agent promoting secretion and/or suppressing decrease of adiponectin, and a eating and drinking product and a feed promoting secretion and/or suppressing decrease of adiponectin, having as an active component a culture supernatant of *Streptococcus*, *Lactobacillus*, *Propionibacterium*, yeast, *Leuconostoc*, and *Lactococcus*.

7 Claims, 1 Drawing Sheet

(56) References Cited

OTHER PUBLICATIONS

"How Do You Treat Metabolic Syndrome" website (https://web.archive.org/web/20071107204753/http://www.webmd.com/heart/metabolic-syndrome/how-do-you-treat-metabolic-syndrome—Internet archived version from Nov. 7, 2007).*
International Search Report for PCT/JP2009/054973, mailed Jun. 23, 2009.
International Preliminary Report on Patentability for PCT/JP2009/054973, mailed Sep. 16, 2010.
Supplementary European Search Report issued with respect to patent family member European Patent App. No. 09718558.1, dated Apr. 5, 2012.
Database WPI, Week 200651, Thomson Scientific, London, GB; AN 2006-497083, XP002671059, 2006.
Database WPI, Week 200746, Thomson Scientific, London, GB; AN 2007-472892, XP002671060, 2007.
Database WPI, Week 200619, Thomson Scientific, London, GB; AN 2006-178244, XP002671061, 2006.
Stark et al., "Nucleotide sequence transcription analysis of a linear DNA plasmid associated with the killer character of the yeast *Kluyveromyces lactis*," *Nucleic Acids Research* 12(15):6011-6030, 1984.
Stark et al., "The killer toxin of *Kluyveromyces lactis*: characterization of the toxin subunits and identification of the genes which encode them," *The EMBO Journal* 5(8):1995-2002, 1986.
Toshifumi Azuma, *Kanzo*, vol. 45 (2004) No. 2, pp. 87-89.
Aimin Xu et al., "The fat-derived hormone adiponectin alleviates alcoholic and nonalcoholic fatty liver diseases in mice" *J Clin Invest,* 2003, 112(1), pp. 91-100.
Japanese Office Action issued with respect to Japanese Patent Application No. JP 2010-535135, mailed Oct. 22, 2013, along with an English language translation.
Korean Office Action issued with respect to application No. 10-2010-7018560,mail date is Jun. 28, 2016.

* cited by examiner

AGENTS FOR PROMOTING SECRETION AND/OR SUPPRESSING DECREASE OF ADIPONECTIN

TECHNICAL FIELD

The present invention relates to an agent for promoting secretion and/or suppressing decrease of adiponectin, containing culture supernatants of *Streptococcus, Lactobacillus, Propionibacterium*, yeast, *Leuconostoc*, and *Lactococcus* as active ingredients, new foods and drinks to which an action promoting secretion and/or suppressing decrease of adiponectin is imparted, and new feeds to which an action of promoting secretion and/or suppressing decrease of adiponectin is imparted. Ingestion of the agents of the present invention can promote secretion and/or suppress decrease of adiponectin from fat tissues. A decrease in adiponectin secretion causes onset and exacerbation of metabolic syndrome that is resulted from a combination of hypertension, hyperlipemia, diabetes mellitus, etc, so the present invention is effective for its prevention and remedy.

BACKGROUND ART

Enlargement of fat cells and excessive accumulation of visceral fats triggers the onset of complex lesions of hypertension and hyperlipemia, diabetes mellitus, etc. These lesions are totally called metabolic syndrome, and recently have a large problem in human health, whereby its measures become an urgent business.

Visceral fat tissues secret endocrine components such as adiponectin, a plasminogen activator inhibitor, a tumor necrosis factor (TNF-α) and leptin and contribute to the maintenance of homeostasis in living bodies. However, when fat cells swell, the secretion of these components become abnormal and then excessive or insufficient. Recent studies show that breakdown of this balance is deeply involved in the onset or exacerbation of metabolic syndrome. Of these, the abnormal secretion of adiponectin is thought to have the largest effect (e.g., see non-patent document 1).

A is a molecule having 244 amino acids, is secreted from fat tissues, and exhibits not only the effect of insulin resistance improvement but also the effect of improving fat-burning in the liver and muscles. In addition, adiponectin is clarified to have the function of improving intake of glucose and fatty acid in blood into cells. Accumulation of fats in muscles and liver or the like worsens the intake of sugars leading to diabetes mellitus. However, usually, adiponectin seems to decompose fats and sugars that are temporarily excessive to maintain the nutrition balance in the body. When obesity progresses, the function of fat cells secreting adiponectin is weakened and the nutrition balance in the body is said to be broken. In this way, normality of adiponectin secretion is expected to have the effect of totally improving symptoms of metabolic syndrome such as hypertension, lipid dysbolism and diabetes mellitus.

Drugs or artificial compounds having the effect of increasing adiponectin are searched, but since there is the possibility of having side effects, attention has been paid to studies of food ingredients having functions like restraining the development of symptoms through eating habits as much as possible. As many extracts derived from plants are disclosed that include apple extracts (e.g., see patent document 1), spent hop extracts (e.g., see patent document 2), green tea catechin (e.g., see patent document 3), rice bran extracts (e.g., see patent document 4), turmeric extracts (e.g., see patent document 5) and the like. However, these have complicated extraction conditions and restraint of obtainment of extract raw materials, and exhibit decreases in taste when added to foods, their applicability as raw materials of formulations or eating and drinking products is questionable.

On the other hand, foods to which fermentation by lactic acid bacteria is applied are widely spread including cheeses and yoghurts and pickles and can be relatively inexpensively supplied and also have been produced in quantities in the world from old times due to their high acceptability. Additionally, Propionibacteraceae and yeast have been utilized for production of cheeses from old times and have contributed to fermentation of characteristic flavors (e.g., see non-patent document 2). These lactic acid bacteria, Propionibacteraceae, and yeast produce many decomposition products and metabolic products. Of these, although many health functional components have been found, still function-unknown components are thought to be present.

The present inventors have found that a peptide derived from milk protein separated from lactic acid bacteria aged cheese has the effect of promoting adiponectin production (e.g., see patent document 6). In addition, the present applicants have found that lactic acid bacteria cultures, particularly the cultures of *Lactobacillus gasseri* and *Lactobacillus helveticus*, using defatted milk culture media, have the effect of promoting increase and/or suppressing decrease of blood concentration of adiponectin (Japanese Patent Application No. 2006-244377).

Lactic acid bacteria are known to have prevention actions of pathogen infection (e.g., see patent document 7), prevention actions of inflammatory bowel disease and irritable bowel syndromes (e.g., see patent document 8), bone resorption suppression (e.g., see patent document 9), immunological enhancement actions (e.g., see patent document 10), prevention actions of diabetes mellitus complication (e.g., see patent document 11) and suppression actions of serum cholesterol increase (e.g., see patent document 12). However, culture supernatants which are liquid components prepared by removal of milk protein precipitates or bacterium components from cultures of microbes such as not only lactic acid bacteria but Propionibacteraceae and yeast are not known at all to have the effect of increasing adiponectin alone.

Milk protein precipitates and bacterium components coagulated by fermentation have a large effect on tastes of milk products, and sometimes deteriorate the qualities, lowering the product values. Technologies for removing precipitates from milk fermentation materials have also been developed (e.g., see patent document 13), and culture supernatants of milk fermentation materials that impart good tastes and high acceptability to foods have high industrial applicability as food raw materials.

[Patent Citation 1]
JP-A-2006-193502
[Patent Citation 2]
JP-A-2006-193501
[Patent Citation 3]
JP-A-2006-131512
[Patent Citation 4]
JP-A-2005-068132
[Patent Citation 5]
JP-A-2005-060308
[Patent Citation 6]
JP-A-2007-254448
[Patent Citation 7]
JP-A-8-268899

[Patent Citation 8]
JP-A-2003-095963
[Patent Citation 9]
JP-A-2004-315477
[Patent Citation 10]
JP-A-2006-069993
[Patent Citation 11]]
JP-A-2003-252770
[Patent Citation 12]
JP-A-2003-306436
[Patent Citation 13]
JP-A-6-319477
[Non Patent Citation 1]
J. Clin. Invest., 116:1784-1792
[Non Patent Citation 2]
P. F. Fox, P. L. H. McSweeney, T. M. Cogan and T. P. Guinee, "CHEESE: Chemistry, Physics and Microbiology Third Edition Volume 1 General Aspects", Academic Press (2004)

DISCLOSURE OF INVENTION

Technical Problem

The object of the present invention is to provide culture supernatants of Streptococcus, *Lactobacillus, Propionibacterium*, yeast, *Leuconostoc*, and *Lactococcus* having excellent applicability and universal use as food raw materials and being effective for the prevention and therapy of metabolic syndrome by promoting secretion of adiponectin in living bodies. In the case of some of the microorganisms, which have been the object of this study, the culture or the cell itself of these microorganisms have been found to be effective as agents for the prevention and therapy of metabolic syndrome by promoting secretion of adiponectin in living bodies.

Technical Solution

The present inventors have diligently studied and revealed that the culture supernatants of *Streptococcus, Lactobacillus, Propionibacterium*, yeast, *Leuconostoc*, and *Lactococcus* exhibits the extremely high effect promoting secretion and/or suppressing decrease of adiponectin, having led to the completion of the present invention.

Hence, the present invention is an invention having the constitutions below.

(1) An agent for promoting secretion and/or suppressing decrease of adiponectin, comprising a culture supernatant of any one of microorganisms selected from the group consisting of *Streptococcus, Lactobacillus, Propionibacterium*, yeast, *Leuconostoc*, and *Lactococcus as an active ingredient*.

(2) An eating and drinking product for promoting secretion and/or suppressing decrease of adiponectin, comprising a culture supernatant of any one of microorganisms selected from the group consisting of *Streptococcus, Lactobacillus, Propionibacterium*, yeast, *Leuconostoc*, and *Lactococcus* as an active ingredient.

(3) A feed for promoting secretion and/or suppressing decrease of adiponectin, comprising a culture supernatant of any one of microorganisms selected from the group consisting of *Streptococcus, Lactobacillus, Propionibacterium*, yeast, *Leuconostoc*, and *Lactococcus* an active ingredient.

(4) An agent for promoting secretion and/or suppressing decrease of adiponectin, comprising a culture and/or cell of any one of microorganisms selected from the group consisting of *Propionibacterium* and yeast as an active ingredient.

(5) An eating and drinking product for promoting secretion and/or suppressing decrease of adiponectin, comprising a culture and/or cell of any one of microorganisms selected from the group consisting of *Propionibacterium* and yeast as an active ingredient.

(6) A feed for promoting secretion and/or suppressing decrease of adiponectin, comprising a culture and/or cell of any one of microorganisms selected from the group consisting of *Propionibacterium* and yeast as an active ingredient.

Advantageous Effects

An agent for promoting secretion and/or suppressing decrease of adiponectin, eating and drinking products and feeds to which actions promoting secretion and/or suppressing decrease of adiponectin are imparted are effective for the prevention and therapy of metabolic syndrome that is said to develop due to a decrease in adiponectin in blood. In addition, an agent promoting secretion and/or suppressing decrease of adiponectin, eating and drinking products and feeds to which actions promoting secretion and/or suppressing decrease of adiponectin are imparted use a culture supernatant of *Streptococcus, Lactobacillus, Propionibacterium*, yeast, *Leuconostoc*, and *Lactococcus*, and thus have features of having excellent applicability and universal use as highly pure food materials and enabling a large amount of supply at a relatively inexpensive price and also having extremely high safety.

BEST MODE FOR CARRYING OUT THE INVENTION

The present inventors have been selecting strains, which are excellent in flavors and physical properties when applied to foods, from milk products and a large number of lactic acid bacteria derived from human, *Propionibacterium* and yeast. Furthermore, they have been capable of selecting *Streptococcus thermophilus* as *Streptococcus, Lactobacillus* spp., *Lactobacillus delbreuckii* subsp. *bulgaricus, Lactobacillus acidophilus, Lactobacillus paracasei* and *Lactobacillus fermentum* as *Lactobacillus, Propionibacterium freudenreichii* as *Propionibacterium, Kluyveromyces lactis* and *Saccharomyces cervisiae* as yeast, *Leuconostoc* spp., *Leuconostoc mescenteroides* and *Leuconostoc lactis* as *Leuconostoc, Lactococcus lactis* subsp. *lactis* and *Lactococcus lactis* subsp. *cremoris* as *Lactococcus* under conditions in which the culture supernatants of the stains have the effect of promoting secretion and/or suppressing decrease of adiponectin. Furthermore, they have been capable of selecting *Streptococcus thermophilus* T004593 (CNCM I-3934), *Lactobacillus* spp. T003769 (CNCM I-3932), *Propionibacterium freudenreichii* T004406 (CNCM I-3931), *Kluyveromyces lactis* T001985 (CNCM I-3935), *Leuconostoc* spp. T003986 (CNCM I-3933), *Lactococcus lactis* T004455 (CNCM I-3930), *Lactobacillus delbreuckii* subsp. *bulgaricus* T003658 (CNCM I-4090), *Lactobacillus fermentum* T003766 (CNCM I-4091), *Lactobacillus gasseri* SBT-0274 (BP-11039), *Lactobacillus gasseri* SBT-2056 (BP-11038), *Lactobacillus acidophilus* SBT-2062 (BP-11075), *Lactobacillus paracasei* SBT-2558 (BP-11076), *Streptococcus ther-* mophilus ATCC-19258T, *Saccharomyces cervisiae* JCM-7255T, *Propionibacterium freudenreichii* subsp. *freudenreichii* DSM-20271T, *Kluyveromyces lactis* NBRC-1090T, *Lactobacillus brevis* JCM-1059T, *Lactobacillus plantarum* JCM-1149, *Propionibacterium freudenreichii* subsp. *shermanii* DSM-4902T, *Kluyveromyces marxianus* JCM-1630T.

These CNCM strains are deposited with Institut Pasteur in France and AP strains are deposited with International Patent Organism Depositary (IPOD) in Japan, which are the International Authority Depository. Other standard strains can be obtained from public culture collection centers such as American Type Culture Collection (ATCC) or Japan Collection of Microorganisms (JCM) or German Collection of Microorganisms (DSMZ) or NITE Biological Resource Center (NBRC).

It is not known at all that *Streptococcus, Lactobacillus, Propionibacterium*, yeast, *Leuconostoc*, and *Lactococcus* show the effects of such promoting secretion and/or suppressing decrease of adiponectin only by their culture supernatants excluding their bacterium bodies and the present inventors have clarified the effects for the first time.

It is not known at all that a culture and/or cell of a microorganism selected from: *Propionibacterium freudenreichii* T004406 (CNCM I-3931), *Kluyveromyces lactis* T001985 (CNCM I-3935), *Saccharomyces cervisiae* JCM-7255T, *Propionibacterium freudenreichii* subsp. *freudenreichii* DSM-20271T, *Kluyveromyces lactis* NBRC-1090T, *Propionibacterium freudenreichii* subsp. *shermanii* DSM-4902T, *Kluyveromyces marxianus* JCM-1630T, show the effects of promoting secretion and/or suppressing decrease of adiponectin and the present inventors have clarified the effects for the first time.

Next, a method of culturing these lactic acid bacteria, *Propionibacterium* and yeast will be described. A variety of culture media can be used such as a milk medium, a culture medium containing milk components or a semisynthetic medium not containing milk component, and a culture medium to which a whey powder is added as a milk component is particularly preferred. The culture method performs a stationary culture or a neutralization culture that controls pH to be constant, and the culture method is not particularly limited so long as it has conditions in which bacteria are well grown. The milk proteins and bacterium components are removed from the resulting cultures by means of a method such as centrifugation or filtration to be able to obtain culture supernatants.

An agent promoting secretion and/or suppressing decrease of adiponectin of the present invention has a cell or culture or culture supernatant obtained as described above as an active ingredient. The culture supernatant may be directly used or its dried powder may be used as an active ingredient. The drying method is not particularly limited and a freeze-drying method of restraining the deterioration of ingredients is preferred. This powder is mixed with an appropriate excipient such as milk sugar to make a powder, tablet, pill, capsule, syrup or the like, thereby being capable of formulation. These are preferably orally administered.

In addition, the present invention is an eating and drinking product to which actions promoting secretion and/or suppressing decrease of adiponectin is imparted, having a culture supernatant obtained as described above as an active ingredient. Any eating and drinking products are acceptable, and a culture supernatant and an eating and drinking product blended with a culture supernatant itself are also acceptable. A culture supernatant or its dried material may be added to any eating and drinking products during eating, may be added to a product during a step of manufacturing an eating and drinking product, or may be blended with a raw material. The examples of eating and drinking products can include foods such as milk beverages, fermented milk, fruit juice drinks, jellies, candies, egg processed products such as mayonnaise, confectioneries such as butter cakes and breads. Additionally, the examples that can be illustrated include products prepared by blending a culture supernatant or its dried material with a nutrition composition for infants and low-birth-weight infants as well as various powder milks.

Moreover, the present invention is a feed to actions promoting secretion and/or suppressing decrease of adiponectin is imparted, having a culture supernatant obtained as described above as an active ingredient. As a domestic animal feed, like the above eating and drinking products, a culture supernatant or its dried material may be blended with any feeds, or may be added to a raw material during their manufacturing step.

In the present invention, in the case of normal adults, a dose, an amount of blending or the like may be adjusted in such a way that a culture supernatant of *Streptococcus, Lactobacillus, Propionibacterium*, yeast, *Leuconostoc*, and *Lactococcus* can be ingested in amount of from 10 to 200 g per day or its dried material can be ingested in an amount of from 0.5 to 50 g, in order to facilitate the actions promoting secretion and/or suppressing decrease of adiponectin.

The present invention will be described in more detail by way of example and testing example hereinafter; however, these are simply illustrations and the invention is by no means limited by these.

[Mood for the Invention 1]

(Preparation 1 of Culture Supernatant)

A reduced whey medium (containing 13 weight % whey powder and 0.5 weight % yeast extract) was sterilized at 95° C. for 30 minutes and then *Streptococcus thermophilus* T004593 (CNCM I-3934), *Lactobacillus* spp. T003769 (CNCM I-3932), *Propionibacterium freudenreichii* T004406 (CNCM I-3931), *Kluyveromyces lactis* T001985 (CNCM I-3935), *Leuconostoc* spp. T003986 (CNCM I-3933), *Lactococcus lactis* T004455 (CNCM I-3930), *Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* SBT-19258T, *Saccharomyces cervisiae* JCM-7255T, *Propionibacterium freudenreichii* subsp. *freudenreichii* DSM-20271T, *Kluyveromyces lactis* NBRC-1090T *Lactobacillus brevis* JCM-1059T, *Lactobacillus plantarum* JCM-1149, *Propionibacterium freudenreichii* subsp. *shermanii* DSM-4902T, *Kluyveromyces marxianus* JCM-1630T was inoculated thereinto and the strain was cultured at 37° C. for 16 hours (*Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus paracasei* SBT-2558 (BP-11076), *Lactobacillus gasseri* SBT-0274 (BP-11039), *Streptococcus thermophilus* ATCC-19258T, *Lactobacillus brevis* JCM-1059T, *Lactobacillus plantarum* JCM-1149) or at 30° C. for 16 hours (*Saccharomyces cervisiae* JCM-7255T, *Propionibacterium freudenreichii* subsp. *freudenreichii* DSM-20271T, *Kluyveromyces lactis* NBRC-1090T, *Propionibacterium freudenreichii* subsp. *shermanii* DSM-4902T, *Kluyveromyces marxianus* JCM-1630T). The resulting culture material was centrifuged at 3,500 rpm for 20 minutes to obtain a precipitate removed culture supernatant. This can be directly used as an agent promoting secretion and/or suppressing decrease of adiponectin of the present invention.

[Mood for the Invention 2]

(Preparation 2 of Culture Supernatant)

A reduced defatted milk medium (containing 13 weight % of a milk serum powder and 0.5 weight % of a yeast extract) was sterilized at 95° C. for 30 minutes and then *Streptococcus thermophilus* T004593 (CNCM I-3934), *Lactobacillus* spp. T003769 (CNCM I-3932), *Propionibacterium freudenreichii* T004406 (CNCM I-3931), *Kluyveromyces lactis* T001985 (CNCM I-3935), *Leuconostoc* spp. T003986 (CNCM I-3933), *Lactococcus lactis* T004455 (CNCM I-3930), *Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Saccharomyces cervisiae* JCM-7255T, *Propionibacterium freudenreichii* subsp. *freudenreichii* DSM-20271T, *Kluyveromyces lactis* NBRC-1090T *Lactobacillus brevis* JCM-1059T, *Lactobacillus plantarum* JCM-1149, *Propionibacterium freudenreichii* subsp. *shermanii* DSM-4902T, *Kluyveromyces marxianus* JCM-1630T was inoculated thereinto and the strain was cultured at 37° C. for 16 hours (*Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Lactobacillus brevis* JCM-1059T, *Lactobacillus plantarum* JCM-1149) or at 30° C. for 16 hours (*Saccharomyces cervisiae* JCM-7255T, *Propionibacterium freudenreichii* subsp. *freudenreichii* DSM-20271T, *Kluyveromyces lactis* NBRC-1090T, *Propionibacterium freudenreichii* subsp. *shermanii* DSM-4902T, *Kluyveromyces marxianus* JCM-1630T). The resulting culture material was centrifuged at 3,500 rpm for 20 minutes to obtain a precipitate removed culture supernatant. This can be directly used as an agent for secretion promotion and/or decrease suppression of adiponectin of the present invention.

Testing Example 1

Fat Cell Administration Experiment

The culture supernatant obtained in Example 1 was experimentally administered to a primary culture visceral fat cell. The experiment was carried out using a primary culture visceral fat cell of a rat (VAC01, Cell Garage Co., Ltd.) and a visceral fat cell differentiation derivation medium (Cell Garage Co., Ltd.). The day on which freeze-stored cells were melted according to the protocol of Cell Garage Co., Ltd. and the cells were seeded in a 24-well plate was set to be day 0. On day 5 on which the secretion of adiponectin becomes active, a reduced whey medium culture supernatant was added to the medium. As a comparison reference, a medium added a reduced whey medium was prepared. At 37° C. and a carbon dioxide partial pressure of 0.5%, the cells were cultured for two hours and the medium was collected.

The concentration of adiponectin secreted into the medium was determined using an AELISA kit (Otsuka Pharmaceutical Co., Ltd.). The measurement result was standardized by means of the amount of DNA extracted from each well.

(Experimental. Results of Fat Cell Administration)

Figure 1:
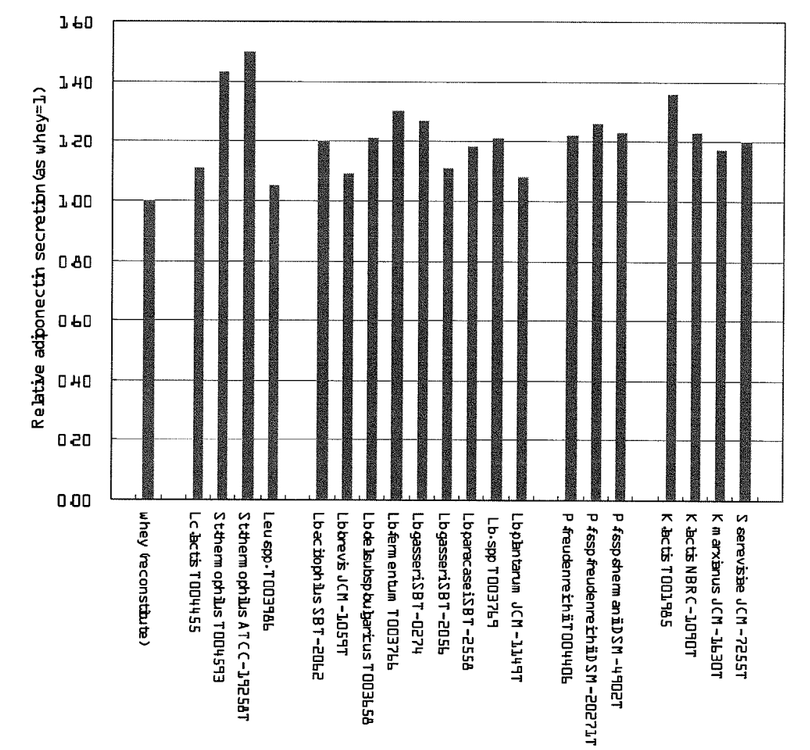
FIG. 1 indicates the measurements of the concentrations of adiponectin. (Testing Example 1)

FIG. 1 shows the measurement results of the concentrations of adiponectin when the reduced whey media were used for the culture media of *Streptococcus thermophilus* T004593 (CNCM I-3934), *Lactobacillus* spp. T003769 (CNCM I-3932), *Propionibacterium freudenreichii* T004406 (CNCM I-3931), *Kluyveromyces lactis* T001985 (CNCM I-3935), *Leuconostoc* spp. T003986 (CNCM I-3933), *Lactococcus lactis* T004455 (CNCM I-3930), *Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Saccharomyces cervisiae* JCM-7255T, *Propionibacterium freudenreichii* subsp. *freudenreichii* DSM-20271T, *Kluyveromyces lactis* NBRC-1090T, *Lactobacillus brevis* JCM-1059T, *Lactobacillus plantarum* JCM-1149, *Propionibacterium freudenreichii* subsp. *shermanii* DSM-4902T, *Kluyveromyces marxianus* JCM-1630T. As compared with the amount of production of adiponectin when the reduced whey medium was added to the fat cell, the culture supernatant of *Streptococcus thermophilus* T004593 (CNCM I-3934) was increased 1.43-fold, the culture supernatant of *Lactobacillus* spp. T003769 (CNCM I-3932) was increased 1.21-fold, the culture supernatant of *Propionibacterium freudenreichii* T004406 (CNCM I-3931) was increased 1.22-fold, the culture supernatant of *Kluyveromyces lactis* T001985 (CNCM I-3935) was increased 1.36-fold, the culture supernatant of *Leuconostoc* spp. T003986 (CNCM I-3933) was increased 1.05-fold, the culture supernatant of *Lactococcus lactis* T004455 (CNCM I-3930) was increased 1.11-fold, the culture supernatant of *Lactobacillus delbreuckii* subsp. *bulgaricus* T003658 (CNCM I-4090) was increased 1.21-fold, the culture supernatant of *Lactobacillus fermentum* T003766 (CNCM I-4091) was increased 1.30-fold, the culture supernatant of *Lactobacillus acidophilus* SBT-2062 (BP-11075) was increased 1.20-fold, the culture supernatant of *Lactobacillus paracasei* SBT-2558 (BP-11076) was increased 1.18-fold, the culture supernatant of *Lactobacillus gasseri* SBT-0274 (BP-11039) was increased 1.27-fold, the culture supernatant of *Lactobacillus gasseri* SBT-2056 (BP-11038) was increased 1.11-fold, the culture supernatant of *Streptococcus thermophilus* ATCC-19258T was increased 1.50-fold, the culture supernatant of *Saccharomyces cervisiae* JCM-7255T was increased 1.20-fold, the culture supernatant of *Propionibacterium freudenreichii* subsp. *freudenreichii* DSM-20271T was increased 1.26-fold, the culture supernatant of *Kluyveromyces lactis* NBRC-1090T was increased 1.23-fold, the culture supernatant of *Lactobacillus brevis* JCM-1059T was increased 1.09-fold, the culture supernatant of *Lactobacillus plantarum* JCM-1149 was increased 1.08-fold, the culture supernatant of *Propionibacterium freudenreichii* subsp. *shermanii* DSM-4902T was increased 1.23-fold, and the culture supernatant of *Kluyveromyces marxianus* JCM-1630T was increased 1.17-fold.

The above results suggest that the culture supernatants of *Streptococcus thermophilus* T004593 (CNCM I-3934), *Lactobacillus* spp. T003769 (CNCM I-3932), *Propionibacterium freudenreichii* T004406 (CNCM I-3931), *Kluyveromyces lactis* T001985 (CNCM I-3935), *Leuconostoc* spp. T003986 (CNCM I-3933), *Lactococcus lactis* T004455

(CNCM I-3930), *Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Saccharomyces cervisiae* JCM-7255T, *Propionibacterium freudenreichii* subsp. *freudenreichii* DSM-20271T, *Kluyveromyces lactis* NBRC-1090T, *Lactobacillus brevis* JCM-1059T, *Lactobacillus plantarum* JCM-1149, *Propionibacterium freudenreichii* subsp. *shermanii* DSM-4902T, *Kluyveromyces marxianus* JCM-1630T have actions to facilitate remarkably the secretion of adiponectin to fat cells and that their actions are attributed not to a reduced milk serum medium but to a component produced from each bacterium.

[Mood for the Invention 3]
(Production of Tablet)

A reduced whey medium (formulating 13 weight % whey powder and 0.5 weight % yeast extract) was sterilized at 95° C. for 30 minutes and then *Streptococcus thermophilus* T004593 (CNCM I-3934), *Lactobacillus* spp. T003769 (CNCM I-3932), *Propionibacterium freudenreichii* T004406 (CNCM I-3931), *Kluyveromyces lactis* T001985 (CNCM I-3935), *Leuconostoc* spp. T003986 (CNCM I-3933), *Lactococcus lactis* T004455 (CNCM I-3930), *Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Saccharomyces cervisiae* JCM-7255T, *Propionibacterium freudenreichii* subsp. *freudenreichii* DSM-20271T, *Kluyveromyces lactis* NBRC-1090T, *Lactobacillus brevis* JCM-1059T, *Lactobacillus plantarum* JCM-1149, *Propionibacterium freudenreichii* subsp. *shermanii* DSM-4902T, *Kluyveromyces marxianus* JCM-1630T was inoculated thereinto and the strain was cultivated 37° C. for 16 hours (*Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Lactobacillus brevis* JCM-1059T, *Lactobacillus plantarum* JCM-1149) or at 30° C. for 16 hours (*Saccharomyces cervisiae* JCM-7255T, *Propionibacterium freudenreichii* subsp. *freudenreichii* DSM-20271T, *Kluyveromyces lactis* NBRC-1090T, *Propionibacterium freudenreichii* subsp. *shermanii* DSM-4902T, *Kluyveromyces marxianus* JCM-1630T). The resulting culture material was centrifuged at 3,500 rpm for 20 minutes to obtain a precipitate removed culture supernatant. This was subjected to freeze-drying treatment to obtain a culture supernatant powder. With 1 part of this culture supernatant powder was mixed 4 parts of non-fat dry milk. This mixed powder was tablet-made gram by gram by the usual method by means of a tablet making machine to prepare agents promoting secretion and/or suppressing decrease of adiponectin containing 200 mg of the culture supernatant of Streptococcus, Lactobacillus, Propionibacterium, yeast, Leuconostoc, and Lactococcus.

[Mood for the Invention 4]
(Production of Powder)

*Streptococcus thermophilus* T004593 (CNCM I-3934), *Lactobacillus* spp. T003769 (CNCM I-3932), *Propionibacterium freudenreichii* T004406 (CNCM I-3931), *Kluyveromyces lactis* T001985 (CNCM I-3935), *Leuconostoc* spp. T003986 (CNCM I-3933), *Lactococcus lactis* T004455 (CNCM I-3930), *Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Saccharomyces cervisiae* JCM-7255T, *Propionibacterium freudenreichii* subsp. *freudenreichii* DSM-20271T, *Kluyveromyces lactis* NBRC-1090T, *Lactobacillus brevis* JCM-1059T, *Lactobacillus plantarum* JCM-1149, *Propionibacterium freudenreichii* subsp. *shermanii* DSM-4902T, *Kluyveromyces marxianus* JCM-1630T was inoculated in 5 L of a reduced whey medium and then the resulting material was stationary-cultured at 37° C. for 16 hours (*Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Lactobacillus brevis* JCM-1059T, *Lactobacillus plantarum* JCM-1149) or at 30° C. for 16 hours (*Saccharomyces cervisiae* JCM-7255T, *Propionibacterium freudenreichii* subsp. *freudenreichii* DSM-20271T, *Kluyveromyces lactis* NBRC-1090T, *Propionibacterium freudenreichii* subsp. *shermanii* DSM-4902T, *Kluyveromyces marxianus* JCM-1630T). After the completion of culture, the material was centrifuged at 7,000 rpm for 15 minutes to obtain a culture supernatant without precipitates. Next, this culture supernatant was mixed with an equivalent amount of a dispersion solvent prepared by blending 10 weight % non-fat dry milk and 1 weight % monosodium glutamate and then the resulting material was adjusted to pH 7 and freeze-dried. The resulting freeze-dried material was granulated with a 60-mesh sieve to produce a culture supernatant freeze-dried material. In accordance with the regulation of "Powders" of The Japanese Pharmacopoeia, Thirteenth Edition, Explanatory of General Rules For Preparations, to 1 g of this culture supernatant freeze-dried material were added 400 g of lactose (Japanese Pharmacopoeia) and 600 g of potato starch (Japanese Pharmacopoeia) and the resulting material was uniformly admixed to obtain an agent promoting secretion and/or suppressing of adiponectin.

[Mood for the Invention 5]
(Production of Capsule)

*Streptococcus thermophilus* T004593 (CNCM I-3934), *Lactobacillus* spp. T003769 (CNCM I-3932), *Propionibacterium freudenreichii* T004406 (CNCM I-3931), *Kluyveromyces lactis* T001985 (CNCM I-3935), *Leuconostoc* spp. T003986 (CNCM I-3933), *Lactococcus lactis* T004455 (CNCM I-3930), *Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Saccharomyces cervisiae* JCM-7255T, *Propionibacterium freudenreichii* subsp. *freudenreichii* DSM-20271T, *Kluyveromyces lactis* NBRC-1090T, *Lactobacillus brevis* JCM-1059T, *Lactobacillus plantarum* JCM-1149, *Propionibacterium freudenreichii* subsp. *shermanii* DSM-4902T, *Kluyveromyces marxianus* JCM-1630T was inoculated in 5 L of a reduced whey medium and then the resulting material was stationary-cultured at 37° C. for 16 hours (*Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Lactobacillus brevis* JCM-1059T, *Lactobacillus plantarum* JCM-1149) or at 30° C. for 16 hours (*Saccharomyces cervisiae* JCM-7255T, *Propionibacterium freudenreichii* subsp. *freudenreichii* DSM-20271T, *Kluyveromyces lactis* NBRC-1090T, *Propionibacterium freudenreichii* subsp. *shermanii* DSM-4902T, *Kluyveromyces marxianus* JCM-1630T). After the completion of culture, the material was centrifuged at 7,000 rpm for 15 minutes to obtain a culture supernatant without precipitates. Next, this culture supernatant was mixed with an equivalent amount of a dispersion solvent prepared by blending 10 weight % non-fat dry milk and 1 weight % monosodium glutamate and then the resulting material was adjusted to pH 7 and freeze-dried. The resulting freeze-dried material was granulated with a 60-mesh sieve to produce a culture supernatant freeze-dried material. The raw materials on the basis of the formulation indicated in Table 1 are admixed and granulated and then loaded into a capsule to produce a capsule for promoting secretion and/or suppressing decrease of adiponectin of the present invention.

TABLE 1

| Culture supernatant freeze-dried material | 20.0 (weight %) |
|---|---|
| Lactose | 24.5 |
| Soluble starch | 55.0 |
| Magnesium stearate | 0.5 |

[Mood for the Invention 6]
(Production of Stick-Shaped Health Food)

*Streptococcus thermophilus* T004593 (CNCM I-3934), *Lactobacillus* spp. T003769 (CNCM I-3932), *Propionibacterium freudenreichii* T004406 (CNCM I-3931), *Kluyveromyces lactis* T001985 (CNCM I-3935), *Leuconostoc* spp. T003986 (CNCM I-3933), *Lactococcus lactis* T004455 (CNCM I-3930), *Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Saccharomyces cervisiae* JCM-7255T, *Propionibacterium freudenreichii* subsp. *freudenreichii* DSM-20271T, *Kluyveromyces lactis* NBRC-1090T, *Lactobacillus brevis* JCM-1059T, *Lactobacillus plantarum* JCM-1149, *Propionibacterium freudenreichii* subsp. *shermanii* DSM-4902T, *Kluyveromyces marxianus* JCM-1630T was inoculated in 5 L of an MRS liquid culture medium (Difco, Inc.) and then the resulting material was stationary-cultivated at 37° C. for 16 hours (*Lactobacillus delbreucus* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Lactobacillus brevis* JCM-1059T, *Lactobacillus plantarum* JCM-1149) or at 30° C. for 16 hours (*Saccharomyces cervisiae* JCM-7255T, *Propionibacterium freudenreichii* subsp. *freudenreichii* DSM-20271T, *Kluyveromyces lactis* NBRC-1090T, *Propionibacterium freudenreichii* subsp. *shermanii* DSM-4902T, *Kluyveromyces marxianus* JCM-1630T). After the completion of cultivation, the material was centrifuged at a revolution of 7,000 rpm for 15 minutes to obtain a culture supernatant without precipitates. Next, this culture supernatant was mixed with an equivalent amount of a dispersion solvent prepared by blending 10 weight % of non-fat dry milk and 1 weight % of monosodium glutamate and then the resulting material was adjusted to a pH of 7 and then freeze-dried. The resulting freeze-dried material was granulated with a 60-mesh sieve to produce a culture supernatant freeze-dried material. To 30 g of a culture supernatant powder *Streptococcus thermophilus* T004593 (CNCM I-3934), *Lactobacillus* spp. T003769 (CNCM I-3932), *Propionibacterium freudenreichii* T004406 (CNCM I-3931), *Kluyveromyces lactis* T001985 (CNCM I-3935), *Leuconostoc* spp. T003986 (CNCM I-3933), *Lactococcus lactis* T004455 (CNCM I-3930), *Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Saccharomyces cervisiae* JCM-7255T, *Propionibacterium freudenreichii* subsp. *freudenreichii* DSM-20271T, *Kluyveromyces lactis* NBRC-1090T, *Lactobacillus brevis* JCM-1059T, *Lactobacillus plantarum* JCM-1149, *Propionibacterium freudenreichii* subsp. *shermanii* DSM-4902T, *Kluyveromyces marxianus* JCM-1630T were added 40 g of a mixture of equivalent amounts of vitamin C and citric acid, 100 g of granulated sugar, and 60 g of a mixture of equivalent amounts of cone starch and lactose and then admixed. The mixture was placed into a stick-shaped bag to produce a stick-shaped health food for promoting secretion and/or suppressing decrease of adiponectin of the present invention.

[Mood for the Invention 7]
(Production of Drink)

*Streptococcus thermophilus* T004593 (CNCM I-3934), *Lactobacillus* spp. T003769 (CNCM I-3932), *Propionibacterium freudenreichii* T004406 (CNCM I-3931), *Kluyveromyces lactis* T001985 (CNCM I-3935), *Leuconostoc* spp. T003986 (CNCM I-3933), *Lactococcus lactis* T004455 (CNCM I-3930), *Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Saccharomyces cervisiae* JCM-7255T, *Propionibacterium freudenreichii* subsp. *freudenreichii* DSM-20271T, *Kluyveromyces lactis* NBRC-1090T, *Lactobacillus brevis* JCM-1059T, *Lactobacillus plantarum* JCM-1149, *Propionibacterium freudenreichii* subsp. *shermanii* DSM-4902T, *Kluyveromyces marxianus* JCM-1630T was inoculated in 5 L of a reduced whey medium and then the resulting material was stationary-cultured at 37° C. for 16 hours (*Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Lactobacillus brevis* JCM-1059T, *Lactobacillus plantarum* JCM-1149) or at 30° C. for 16 hours (*Saccharomyces cervisiae* JCM-7255T, *Propionibacterium freudenreichii* subsp. *freudenre-* ichii DSM-20271 T, *Kluyveromyces lactis* NBRC-1090T, *Propionibacterium freudenreichii* subsp. *shermanii* DSM-4902T, *Kluyveromyces marxianus* JCM-1630T). After the completion of culture, the material was centrifuged at 7,000 rpm for 15 minutes to obtain a culture supernatant without precipitates. The raw materials on the basis of the formulation indicated in Table 2 were admixed and loaded into a container and then heat sterilized to produce a drink for promoting secretion and/or suppressing decrease of adiponectin of the present invention.

TABLE 2

| Culture supernatant | 2.5 (weight %) |
|---|---|
| Sugar | 7.5 |
| Citric add | 0.6 |
| Apple fruit juice | 10.0 |
| Water | 79.4 |

[Mood for the Invention 8]
(Production of Yoghurt)

*Streptococcus thermophilus* T1004593 (CNCM I-3934), *Lactobacillus* spp. T003769 (CNCM I-3932), *Propionibacterium freudenreichii* T004406 (CNCM I-3931), *Kluyveromyces lactis* T001985 (CNCM I-3935), *Leuconostoc* spp. T003986 (CNCM I-3933), *Lactococcus lactis* T1004455 (CNCM I-3930), *Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Saccharomyces cervisiae* JCM-72551, *Propionibacterium freudenreichii* subsp. *freudenreichii* DSM-20271T, *Kluyveromyces lactis* NBRC-1090T, *Lactobacillus brevis* JCM-1059T, *Lactobacillus plantarum* JCM-1149, *Propionibacterium freudenreichii* subsp. *shermanii* DSM-4902T, *Kluyveromyces marxianus* JCM-1630T was cultivated in an MRS liquid culture medium (Difco, Inc.). The culture solution in a logarithmic growth phase was inoculated in an amount of 1% into 13% reduced whey medium (sterilized at 115° C. for 20 minutes) to which a yeast extract was added in an amount of 0.5% to prepare a mother culture. The resulting cultured material was centrifuged at 3,500 rpm for 20 minutes to obtain a culture supernatant without precipitates. The culture supernatant and the starter culture were added to a yogurt mixture heated at 100° C. for 10 minutes in an amount of 2.5% and 3% respectively. The mixture was fermented at 37° C., and was cooled when the lactic acidity reached 0.85 to terminate fermentation to obtain blood adiponectin level increase acceleration and/or decrease inhibition yoghurt according to the present invention.

[Mood for the Invention 9]
(Production of Drinking Yoghurt)

To 43 kg of the yoghurt obtained in Example 8 were added 4 kg of granulated sugar, 3 kg of water and 0.15 kg of pectin and then the resulting material was homogenized to obtain 50 kg of drinking yoghurt for promoting secretion and/or suppressing decrease of A of the present invention. This drinking yoghurt had a mild, preferable taste and a pH of 3.6.

[Mood for the Invention 10]
(Production of Dog Feed)

*Streptococcus thermophilus* T004593 (CNCM I-3934), *Lactobacillus* spp. T003769 (CNCM I-3932), *Propionibacterium freudenreichii* T004406 (CNCM I-3931), *Kluyveromyces lactis* T001985 (CNCM I-3935), *Leuconostoc* spp. T003986 (CNCM I-3933), *Lactococcus lactis* T004455 (CNCM I-3930), *Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Saccharomyces cervisiae* JCM-7255T, *Propionibacterium freudenreichii* subsp. *freudenreichii* DSM-20271T, *Kluyveromyces lactis* NBRC-1090T, *Lactobacillus brevis* JCM-1059T, *Lactobacillus plantarum* JCM-1149, *Propionibacterium freudenreichii* subsp. *shermanii* DSM-4902T, *Kluyveromyces marxianus* JCM-1630T was inoculated in 5 L of an MRS liquid culture medium (Difco, Inc.) and then the resulting material was stationary-cultured at 37° C. for 16 hours (*Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Lactobacillus brevis* JCM-1059T, *Lactobacillus plantarum* JCM-1149) or at 30° C. for 16 hours (*Saccharomyces cervisiae* JCM-7255T, *Propionibacterium freudenreichii* subsp. *freudenreichii* DSM-20271T, *Kluyveromyces lactis* NBRC-1090T, *Propionibacterium freudenreichii* subsp. *shermanii* DSM-4902T, *Kluyveromyces marxianus* JCM-1630T). After the completion of culture, the material was centrifuged at 7,000 rpm for 15 minutes to obtain a culture supernatant without precipitates. Next, this culture supernatant was mixed with an equivalent amount of a dispersion solvent prepared by blending 10 weight % non-fat dry milk and 1 weight % monosodium glutamate and then the resulting material was adjusted to pH 7 and then freeze-dried. The resulting freeze-dried material was granulated with a 60-mesh sieve to produce a culture supernatant freeze-dried material. The raw materials on the basis of the formulation indicated in Table 3 are admixed to produce a dog breeding feed for promoting secretion and/or suppressing decrease of adiponectin of the present invention.

(Production of Natural Cheese)

*Streptococcus thermophilus* T004593 (CNCM I-3934), *Lactobacillus* spp. T003769 (CNCM I-3932), *Propionibacterium freudenreichii* T004406 (CNCM I-3931), *Kluyveromyces lactis* T001985 (CNCM I-3935), *Leuconostoc* spp. T003986 (CNCM I-3933), *Lactococcus lactis* T004455 (CNCM I-3930), *Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* °SBT-2558 (BP-11076), *Lactobacillus gasseri* SBT-0274 (BP-11039), *Lactobacillus gasseri* SBT-2056 (BP-11038), *Streptococcus thermophilus* ATCC-19258T, *Saccharomyces cervisiae* JCM-7255T, *Propionibacterium freudenreichii* subsp. *freudenreichii* DSM-20271T, *Kluyveromyces lactis* NBRC-1090T, *Lactobacillus brevis* JCM-1059T, *Lactobacillus plantarum* JCM-1149, *Propionibacterium freudenreichii* subsp. *shermanii* DSM-4902T, *Kluyveromyces marxianus* JCM-1630T was inoculated in 5 L of an MRS liquid culture medium (Difco, Inc.) and then the resulting material was stationary-cultured at 37° C. for 16 hours (*Lactobacillus delbreuckii* subsp. *bulgaricus* T003658 (CNCM I-4090), *Lactobacillus fermentum* T003766 (CNCM I-4091), *Lactobacillus acidophilus* SBT-2062 (BP-11075), *Lactobacillus paracasei* SBT-2558 (BP-11076), *Lactobacillus gasseri*

SBT-0274 (BP-11039), *Lactobacillus gasseri* SBT-2056 (BP-11038), *Streptococcus thermophilus* ATCC-19258T, *Lactobacillus brevis* JCM-1059T, *Lactobacillus plantarum* JCM-1149) or at 30° C. for 16 hours (*Saccharomyces cervisiae* JCM-7255T, *Propionibacterium freudenreichii* subsp. *freudenreichii* DSM-20271T, *Kluyveromyces lactis* NBRC-1090T, *Propionibacterium freudenreichii* subsp. *shermanii* DSM-4902T, *Kluyveromyces marxianus* JCM-1630T). After the completion of culture, the material was centrifuged at 7,000 rpm for 15 minutes to obtain a culture supernatant without precipitates. Raw material milk of which the fat percentage was adjusted was subjected to plate pasteurization at 75° C. for 15 seconds. After cooling the raw material milk to 30° C., calcium chloride (0.01%) was added. A commercially available lactic acid bacteria starter (manufactured by Christian Hansen) (1.7%) and the culture supernatant obtained was added to the raw material milk (2.5%). After the addition of rennet (0.003%) to coagulate the milk, the resulting product was cut. The cut product was stirred until the pH reached 6.1 to 6.2, and whey was discharged to obtain curds. The curds were placed in a mold and then compressed. Salt was then added to the resulting product to obtain blood adiponectin level increase acceleration and/or decrease inhibition natural cheese according to the present invention.

TABLE 3

| Culture supernatant freeze-dried material | 2.5 (weight %) |
|---|---|
| Non-fat dry milk | 13.5 |
| Soybean cake | 12.0 |
| Soybean oil | 4.0 |
| Corn oil | 2.0 |
| Palm oil | 27.0 |
| Corn starch | 14.0 |
| Wheat flour | 9.0 |
| *Streptococcus thermophilus* | 2.0 |
| Vitamin mixture | 9.0 |
| Mineral mixture | 2.0 |
| Cellulose | 3.0 |

[Reference to Deposited Biological Materials]

(1)
i. Name and address of depository institution at which the biological material of interest is deposited.
Collection Nationale de Cultures de Microorganismes (CNCM)
Institut Pasteur 25 Rue du Docteur Roux 75724 Paris Cedex 15, France
ii. Date when the biological material was deposited to the depository institution of i.
Mar. 3, 2008
iii. Accession number for the deposition assigned by the depository institution of i.
CNCM I-3930

(2)
i. Name and address of depository institution at which the biological material of interest is deposited.
Collection Nationale de Cultures de Microorganismes (CNCM)
Institut Pasteur 25 Rue du Docteur Roux 75724 Paris Cedex 15, France
ii. Date when the biological material was deposited to the depository institution of i.
Mar. 3, 2008
iii. Accession number for the deposition assigned by the depository institution of i.
CNCM I-3931

(3)
i. Name and address of depository institution at which the biological material of interest is deposited.
Collection Nationale de Cultures de Microorganismes (CNCM)
Institut Pasteur 25 Rue du Docteur Roux 75724 Paris Cedex 15, France
ii. Date when the biological material was deposited to the depository institution of i.
Mar. 3, 2008
iii. Accession number for the deposition assigned by the depository institution of i.
CNCM I-3932

(4)
i. Name and address of depository institution at which the biological material of interest is deposited.
Collection Nationale de Cultures de Microorganismes (CNCM)
Institut Pasteur 25 Rue du Docteur Roux 75724 Paris Cedex 15, France
ii. Date when the biological material was deposited to the depository institution of i.
Mar. 3, 2008
iii. Accession number for the deposition assigned by the depository institution of i.
CNCM I-3933

(5)
i. Name and address of depository institution at which the biological material of interest is deposited.
Collection Nationale de Cultures de Microorganismes (CNCM)
Institut Pasteur 25 Rue du Docteur Roux 75724 Paris Cedex 15, France
ii. Date when the biological material was deposited to the depository institution of i.
Mar. 3, 2008
iii. Accession number for the deposition assigned by the depository institution of i.
CNCM I-3934

(6)
i. Name and address of depository institution at which the biological material of interest is deposited.
Collection Nationale de Cultures de Microorganismes (CNCM)
Institut Pasteur 25 Rue du Docteur Roux 75724 Paris Cedex 15, France
ii. Date when the biological material was deposited to the depository institution of i.
Mar. 3, 2008
iii. Accession number for the deposition assigned by the depository institution of i.
CNCM I-3935

(7)
i. Name and address of depository institution at which the biological material of interest is deposited.
Collection Nationale de Cultures de Microorganismes (CNCM)
Institut Pasteur 25 Rue du Docteur Roux 75724 Paris Cedex 15, France
ii. Date when the biological material was deposited to the depository institution of i.
Nov. 25, 2008
iii. Accession number for the deposition assigned by the depository institution of i.
CNCM I-4090

(8)
i. Name and address of depository institution at which the biological material of interest is deposited.
Collection Nationale de Cultures de Microorganismes (CNCM)
Institut Pasteur 25 rue du Docteur Roux 75724 Paris Cedex 15, France
ii. Date when the biological material was deposited to the depository institution of i.
Nov. 25, 2008
iii. Accession number for the deposition assigned by the depository institution of i.
CNCM I-4091
(9)
i. Name and address of depository institution at which the biological material of interest is deposited.
International Patent Organism Depositary, National Institute of Advanced Industrial Science and Technology
Tsukuba Central 6, 1-1-1 Higashi, Tsukuba, Ibaraki, Japan (post code: 305-8566)
ii. Date when the biological material was deposited to the depository institution of i.
Apr. 22, 1986 (original deposit date)
Oct. 9, 2008 (date for transfer to the deposition under Budapest Treaty from the original deposition)
iii. Accession number for the deposition assigned by the depository institution of i.
FERM BP-11038
(10)
i. Name and address of depository institution at which the biological material of interest is deposited.
International Patent Organism Depositary, National Institute of Advanced Industrial Science and Technology
Tsukuba Central 6, 1-1-1 Higashi, Tsukuba, Ibaraki, Japan (post code: 305-8566)
ii. Date when the biological material was deposited to the depository institution of i.
Mar. 15, 2000 (original deposit date)
Oct. 9, 2008 (date for transfer to the deposition under Budapest Treaty from the original deposition)
iii. Accession number for the deposition assigned by the depository institution of i.
FERM BP-11039
(11)
i. Name and address of depository institution at which the biological material of interest is deposited.
International Patent Organism Depositary, National Institute of Advanced Industrial Science and Technology
Tsukuba Central 6, 1-1-1 Higashi, Tsukuba, Ibaraki, Japan (post code: 305-8566)
ii. Date when the biological material was deposited to the depository institution of i.
May 18, 1989 (original deposit date)
Dec. 15, 2008 (date for transfer to the deposition under Budapest Treaty from the original deposition)
iii. Accession number for the deposition assigned by the depository institution of i.
FERM BP-11075
(12)
i. Name and address of depository institution at which the biological material of interest is deposited.
International Patent Organism Depositary, National Institute of Advanced Industrial Science and Technology
Tsukuba Central 6, 1-1-1 Higashi, Tsukuba, Ibaraki, Japan (post code: 305-8566)
ii. Date when the biological material was deposited to the depository institution of i.
Dec. 20, 1990 (original deposit date)
Dec. 15, 2008 (date for transfer to the deposition under Budapest Treaty from the original deposition)
iii. Accession number for the deposition assigned by the depository institution of i.
FERM BP-11076

The invention claimed is:

1. A method for promoting secretion or suppressing decrease of adiponectin in a subject exhibiting metabolic syndrome, said method comprising:
administering an effective amount of
a first culture supernatant of *Kluyveromyces lactis* or *Kluyveromyces marxianus* or
a second culture supernatant of *Propionibacterium*,
as an active ingredient to a subject in recognized need of promoted secretion or suppressed decrease of adiponectin, who is a subject exhibiting metabolic syndrome; and
promoting secretion or suppressing decrease of adiponectin in the subject.

2. A method for accelerating the increase in or suppressing the decrease of adiponectin concentration, said method comprising:
administering an effective amount of a culture supernatant of a microorganism selected from the group consisting of: *Propionibacterium freudenreichii* T004406 (CNCM I-3931), *Propionibacterium freudenreichii* subsp. *freudenreichii* DSM-20271T, and *Propionibacterium freudenreichii* subsp. *shermanii* DSM-4902T as an active ingredient to a subject in recognized need of accelerated increase in or suppressed decrease of adiponectin concentration; and
accelerating the increase in or suppressing the decrease of adiponectin concentration in the subject.

3. A method for accelerating the increase in or suppressing the decrease of adiponectin concentration, said method comprising:
administering an effective amount of a culture supernatant of a microorganism selected from the group consisting of: *Propionibacterium freudenreichii* T004406 (CNCM I-3931), *Kluyveromyces lactis* T001985 (CNCM I-3935), *Propionibacterium freudenreichii* subsp. *freudenreichii* DSM-20271T, *Kluyveromyces lactis* NBRC-1090T, *Propionibacterium freudenreichii* subsp. *shermanii* DSM-4902T, and *Kluyveromyces marxianus* JCM-1630T, as an active ingredient to a subject in recognized need of accelerated increase in or suppressed decrease of adiponectin concentration; and
accelerating the increase in or suppressing the decrease of adiponectin concentration in the subject.

4. A method for promoting secretion or suppressing decrease of adiponectin, said method comprising:
administering an effective amount of a culture supernatant of a microorganism selected from the group consisting of: *Propionibacterium freudenreichii* T004406 (CNCM I-3931), *Kluyveromyces lactis* T001985 (CNCM I-3935), *Propionibacterium freudenreichii* subsp. *freudenreichii* DSM-20271T, *Kluyveromyces lactis* NBRC-1090T, *Propionibacterium freudenreichii* subsp. *shermanii* DSM-4902T, and *Kluyveromyces marxianus* JCM-1630T, as an active ingredient to a subject in recognized need of promoted secretion or suppressed decrease of adiponectin; and
promoting secretion or suppressing decrease of adiponectin concentration in the subject.

5. A method for promoting secretion or suppressing decrease of adiponectin, said method comprising:
administering an effective amount of a culture supernatant of a microorganism selected from the group consisting of: *Propionibacterium freudenreichii* T004406 (CNCM I-3931), *Propionibacterium freudenreichii* subsp. *freudenreichii* DSM-20271T, and *Propionibacterium freudenreichii* subsp. *shermanii* DSM-4902T as an active ingredient to a subject in recognized need of promoted secretion or suppressed decrease of adiponectin; and promoting secretion or suppressing decrease of adiponectin in the subject.

6. The method of claim 1, wherein the first or second culture supernatant is in dry or powder form.

7. The method according to claim 1, said method comprising administering an effective amount of a culture supernatant of *Kluyveromyces lactis* T001985 (CNCM I-3935), *Kluyveromyces lactis* NBRC-1090T, or *Kluyveromyces marxianus* JCM-1630T as an active ingredient.

* * * * *